United States Patent [19]

Kuwada et al.

[11] 4,044,129
[45] Aug. 23, 1977

[54] 4-PYRIDINE CARBONYL PHENYL 1,2,4 TRIAZOLES

[75] Inventors: Yutaka Kuwada, Ashiya; Kanji Meguro, Takarazuka; Hideaki Natsugari, Nishinomiya; Yoshiaki Sato, Kobe; Hiroyuki Tawada, Takatsuki, all of Japan

[73] Assignee: Takeda Chemical Industries, Ltd., Osaka, Japan

[21] Appl. No.: 592,889

[22] Filed: July 3, 1975

[30] Foreign Application Priority Data

July 25, 1974 Japan .................................. 49-85787

[51] Int. Cl.² .................. C07D 413/14; A61K 31/535
[52] U.S. Cl. ................................ 424/248.56; 424/250; 424/263; 424/267; 260/256; 260/4 Q; 260/268 H; 260/293.69; 260/294.8 R; 260/296 R; 544/131
[58] Field of Search .............. 260/247.5, 268, 296, 260/293.69, 247 SE, 268 H, 296 R, 293.69; 424/248, 250, 267, 269, 248.56, 263

[56] References Cited

U.S. PATENT DOCUMENTS

| 3,646,055 | 2/1972 | Hester | 260/239.3 D |
|---|---|---|---|
| 3,749,733 | 7/1973 | Hester | 260/239.3 D |
| 3,813,412 | 5/1974 | Gall et al. | 260/247.5 E |
| 3,856,792 | 12/1974 | Hester | 260/247.5 E |
| 3,879,406 | 4/1975 | Sternbach et al. | 260/296 T |

Primary Examiner—Henry R. Jiles
Assistant Examiner—R. W. Ramsuer
Attorney, Agent, or Firm—Burgess, Ryan and Wayne

[57] ABSTRACT

A novel triazole derivative of the general formula (I):

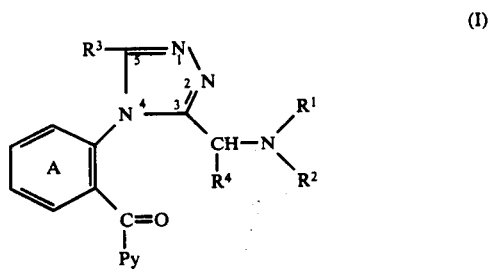

(I)

wherein $R^1$ and $R^2$, which may be the same or different, represent alkyl group or aralkyl group and one of $R^1$ and $R^2$ may be hydrogen atom, or $R^1$ and $R^2$ form a heterocyclic ring together with the nitrogen atom adjacent thereto; $R^3$ represents hydrogen atom or a hydrocarbon residue; $R^4$ represents hydrogen atom or a lower alkyl group; Py represents a pyridyl group; and the ring A is either unsubstituted or substituted by halogen atom, nitro, alkyl, alkoxy or trifluoromethyl group, and pharmaceutically acceptable acid addition salts thereof are found to be useful as medicine in human and animal therapy, as these compounds act on the central nervous as for example, muscle relaxants, anticonvulsants, sedatives, minor tranquilizers, etc.

25 Claims, No Drawings

4-PYRIDINE CARBONYL PHENYL 1,2,4 TRIAZOLES

This invention relates to a novel triazole derivative useful as medicine which is represented by the general formula (I):

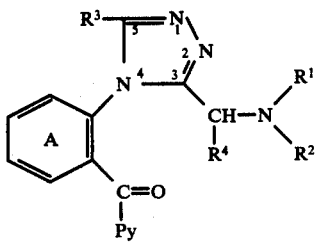

(I)

wherein $R^1$ and $R^2$, which may be the same or different, represent alkyl group or aralkyl group, and one of $R^1$ and $R^2$ may be hydrogen atom, or $R^1$ and $R^2$ form a heterocyclic ring together with the nitrogen atom adjacent thereto; $R^3$ represents hydrogen atom or a hydrocarbon residue; $R^4$ represents hydrogen atom or a lower alkyl group; Py represents a pyridyl group; and the ring A is either unsubstituted or substituted by halogen atom, nitro, alkyl, alkoxy or trifluoromethyl group, and pharmaceutically acceptable acid addition salts thereof and also relates to a process for producing the same.

The compound (I) or its pharmaceutically acceptable acid addition salts has pharmacological effects acting on the central nervous system such as muscle relaxant, anticonvulsant, sedative, antianxiety, tranquilizing and sleep inducing effects and are useful as medicines in human and animal therapy such as muscle relaxants, anticonvulsants, sedatives, antianxiety agents, minor transquilizers and hypnotics.

In the aforesaid formula, the alkyl groups represented by $R^1$ and $R^2$ are preferably lower alkyl groups having 1 to 6 carbon atoms, and the alkyl group may be straight, branched or a $C_3$-$C_6$ cyclic one. Examples of such alkyl groups include methyl, ethyl, propyl, isopropyl, cyclopropyl, butyl, isobutyl sec-butyl, tert-butyl, cyclobutyl, pentyl, hexyl and cycloalkyl compounds such as cyclopropylmethyl, cyclopentyl and cyclohexyl groups. The aralkyl groups represented by $R^1$ and $R^2$ are exemplified by benzyl or phenethyl group. When $R^1$ and $R^2$ form a heterocyclic ring together with the nitrogen atom adjacent thereto, the said heterocyclic ring is preferably a 5- to 7-membered ring, which may contain another 1 to 2 nitrogen and/or oxygen atoms as hetero atom, and examples thereof are pyrrolidine, piperidine, piperazine, morpholine, N-substituted piperazine (e.g. N-methyl piperazine, N-ethyl piperazine, N-(2-hydroxyethyl)piperazine, etc.), homopiperdine, etc.

The hydrocarbon residue represented by $R^3$ includes alkyl, aralkyl and aryl groups. The alkyl groups represented by $R^3$ are preferably those as represented by $R^1$ and $R^2$, i.e. lower alkyl groups having 1 to 6 carbon atoms, and the alkyl group may be straight, branched or cyclic one. The aralkyl groups represented by $R^3$ may also be the same as those represented by $R^1$ and $R^2$. The aryl groups represented by $R^3$ are, for example, phenyl, tolyl, naphthyl, etc. As the residue represented by $R^3$, hydrogen atom or a lower alkyl group having 1 to 3 carbon atoms is particularly preferred.

The lower alkyl group represented by $R^4$ is preferably one having 1 to 4 carbon atoms, and examples thereof are methyl, ethyl, propyl, isopropyl, butyl, isobutyl, sec-butyl, tert-butyl, etc.

When the ring A is substituted by halogen atom or nitro, alkyl, alkoxy or trifluoromethyl group, the number of said substituents is optional at any substitutable positions of the ring A. The halogen atom which is the substituent of the ring A includes fluorine, chlorine, bromine and iodine. The lower alkoxy group which is the substituent of the ring A includes, for example, lower alkoxy groups having 1 to 4 carbon atoms such as methoxy, ethoxy, propoxy and butoxy groups. The alkyl group which is the substituent of the ring A includes, for example, the same lower alkyl groups having 1 to 4 carbon atoms as those represented by $R^2$. As the substituent of the ring A, halogen (particularly bromine or chlorine) is preferable. As the position of the substituent of the ring A in the formula (I), 4-position is preferable, and 4-halogen atom, especially 4-bromo and 4-chloro is preferred as the substituent.

The pyridyl groups represented by Py is represented by the formula

and, among them, 2-pyridyl group is preferred.

The compounds of the formula (I) can be produced by a process which comprises reacting a compound represented by the general formula (II):

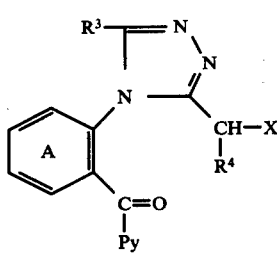

(II)

wherein $R^3$, $R^4$, Py and the ring A are as defined above and X represents halogen atom or a reactive derivative of hydroxy group, with a compound represented by the general formula (III):

(III)

wherein $R^1$ and $R^2$ are as defined above.

In the above formula (II), the halogen atom represented by X includes halogen atoms as exemplified by the substituent on the ring A. The reactive derivative of hydroxy group represented by X is exemplified by sulfoxy(—$OSO_3H$) group, alkyl sulfonyloxy group such as methyl sulfonyloxy group, aryl sulfonyloxy group such as phenyl sulfonyloxy group, p-tolyl sulfonyloxy group, etc.

The process of the present invention is carried out by reacting the compound (II) with the compound (III). The amount of the compound (III) to be used is ordinarily about 1 to 10 moles per mole of the compound (II).

The reaction may proceed in the absence of a solvent, but proceeds more smoothly in the presence of a solvent. Examples of such solvent are alcohols (e.g. methanol, ethanol, propanol, butanol, etc.), aliphatic, aromatic or halogenated hydrocarbons (e.g. benzene, toluene, xylene, chloroform, dichloromethane, etc.), dialkylformamides (e.g. dimethyl- or diethyl-formamide, etc.), ketones (e.g. acetone, methyl ethyl ketone, cyclohexane, etc.), ethers(diethyl ether, dibutyl ether, tetrahydrofuran, dioxane, etc.), pyridine, dimethylsulfoxide, etc. The reaction temperature is suitably within the range of room temperature to 150° C. When a solvent is used, the reaction temperature is usually around the boiling point of the solvent used.

When X of the compound (II) is a halogen atom, a hydrogen halide corresponding to X is produced in this reaction. In order to accept the hydrogen halide, the compound (III) may be used in excess, or alternatively there may be added to the reaction system a suitable basic substance (e.g. a tertiary amine such as triethylamine or pyridine, or an alkali metal carbonate or an alkali metal hydrogen carbonate such as sodium carbonate, potassium carbonate, sodium hydrogen carbonate or potassium hydrogen carbonate). When a compound (II) wherein X is chlorine or bromine, is used as the starting material, the reaction may be more smoothly carried out in the presence of a catalytic or equimolar amount of potassium iodide or sodium iodide.

The compounds (II), which are starting compounds to be used in the present invention, can be synthesized according to, for example, the procedure as shown by the following reaction schemes:

In the above formulae, $R^3$, $R^4$, X, Py and the ring A are as defined above, and $R^5$ represents lower alkyl group (e.g. methyl, ethyl, propyl).

The thus obtained compound (I) of the present invention can be isolated or purified by per se known methods (e.g. column chromatography or recrystallization). Alternatively, it can be purified by recrystallization of an acid addition salt thereof, and if desired this case may be followed by alkali treatment to be converted into free base. Examples of said acid addition salt which is ordinarily water-soluble are salts with inorganic acid (e.g. hydrochloric acid, hydrobromic acid, sulfuric acid, nitric acid and phosphoric acid) or organic acid (e.g. oxalic acid, succinic acid, malonic acid, tartaric acid, fumaric acid, maleic acid, methanesulfonic acid and p-toluenesulfonic acid) which can be prepared in conventional manners. Therefore, the compound of the present invention may be obtained in the form of a pharmaceutically acceptable acid addition salt, e.g. salt with above mentioned acid.

When the object compounds (I) or their pharmaceutically acceptable acid addition salts of the present invention are used as medicines in human and animal therapy such as muscle relaxants, anticonvulsants, sedatives, antianxiety agents, minor tranquilizers or hypnotics, they may be orally or parenterally administered as such or in a suitable form such as powders, granules, tablets, capsules, injections, etc. admixed with pharmaceutically acceptable carriers, excipients or diluents. The dose of the compound (I) or its pharmaceutically acceptable acid addition salt to be administered varies with the kinds of diseases to be treated, the clinical

A:

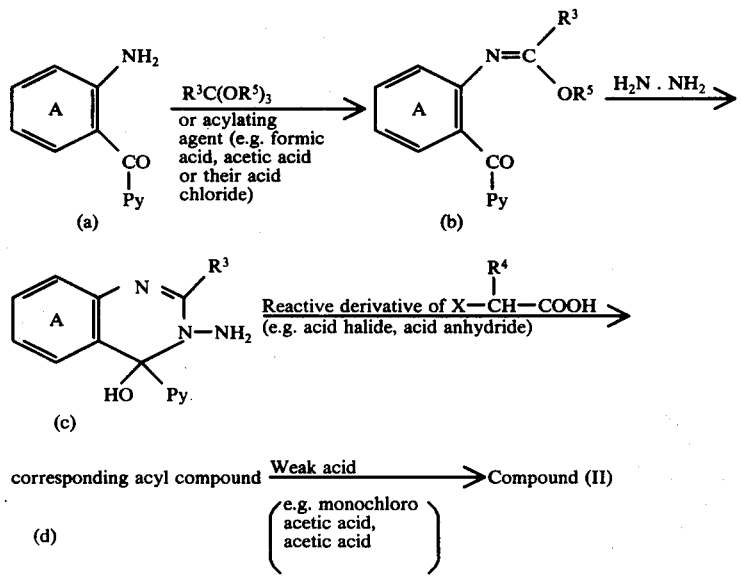

B:

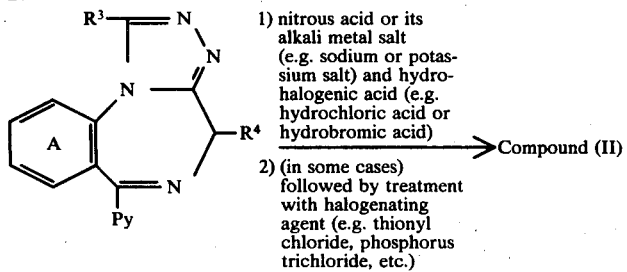

conditions and the kind of the compound to be used, but usually falls within the range of from about 0.1 to 50 mg. (in terms of the free form of the compound (I)) for oral administration for an adult human per day.

Specific compounds as represented by the general formula (I), inclusive of those as shown in Examples which are set forth for illustrative but not limiting purpose, are as follows:

3-methylaminomethyl-4-[2-(2-pyridinecarbonyl)-phenyl]-4H-1,2,4-triazole;
5-methyl-3-methylaminomethyl-4-[2-(2-pyridinecarbonyl)phenyl]-4H-1,2,4-triazole;
3-dimethylaminomethyl-4-[2-(2-pyridinecarbonyl)-phenyl]-4H-1,2,4-triazole;
3-dimethylaminomethyl-5-methyl-4-[2-(2-pyridinecarbonyl)phenyl]-4H-1,2,4-triazole;
3-diethylaminomethyl-4-[2-(2-pyridinecarbonyl)-phenyl]-4H-1,2,4-triazole;
3-dimethylaminomethyl-5-methyl-4-[2-(2-pyridinecarbonyl)phenyl]-4H-1,2,4-triazole;
4-[2-(2-pyridinecarbonyl)phenyl]-3-pyrrolidinomethyl-4H-1,2,4-triazole;
5-methyl-4-[2-(2-pyridinecarbonyl)phenyl]-3-pyrrolidinomethyl-4H-1,2,4-triazole;
3-piperidinomethyl-4-[2-(2-pyridinecarbonyl)phenyl]-4H-1,2,4-triazole;
5-ethyl-3-piperidineomethyl-4-[2-(2-pyridinecarbonyl)-phenyl]-4H-1,2,4-triazole;
5-methyl-3-morpholinomethyl-4-(2-(2-pyridinecarbonyl)phenyl]-4H-1,2,4-triazole;
4-[4-bromo-2-(2-pyridinecarbonyl)phenyl]-3-methylaminomethyl-4H-1,2,4-triazole;
4-[4-bromo-2-(2-pyridinecarbonyl)phenyl]-5-methyl-3-methylaminomethyl-4H-1,2,4-triazole;
4-[4-bromo-2-(2-pyridinecarbonyl)phenyl]-3-dimethylaminomethyl-4H-1,2,4-triazole;
4-[4-bromo-2-(2-pyridinecarbonyl)phenyl]-3-dimethylaminomethyl-5-methyl-4H-1,2,4-triazole;
4-[4-bromo-2-(2-pyridinecarbonyl)phenyl]-5-ethyl-3-dimethylaminomethyl-4H-1,2,4-triazole;
4-[4-bromo-2-(2-pyridinecarbonyl)phenyl]-3-ethylaminomethyl-4H-1,2,4-triazole;
4-[4-bromo-2-(2-pyridinecarbonyl)phenyl]-3-ethylaminomethyl-5-methyl-4H-1,2,4-triazole;
4-[4-bromo-2-(2-pyridinecarbonyl)phenyl]-3-diethylaminomethyl-4H-1,2,4-triazole;
4-[4-bromo-2-(2-pyridinecarbonyl)phenyl]-3-diethylaminomethyl-5-methyl-4H-1,2,4-triazole;
4-[4-bromo-2-(2-pyridinecarbonyl)phenyl]-3-diethylaminomethyl-5-ethyl-4H-1,2,4-triazole;
4-[4-bromo-2-(2-pyridinecarbonyl)phenyl]-3-dipropylaminomethyl-4H-1,2,4-triazole;
4-[4-bromo-2-(2-pyridinecarbonyl)phenyl]-3-diisopropylaminomethyl-4H-1,2,4-triazole;
4-[4-bromo-2-(2-pyridinecarbonyl)phenyl]-3-pyrrolidinomethyl-4H-1,2,4-triazole;
4-[4-bromo-2-(2-pyridinecarbonyl)phenyl]-5-methyl-3-pyrrolidinomethyl-4H-1,2,4-triazole;
4-[4-bromo-2-(2-pyridinecarbonyl)phenyl]-5-ethyl-3-pyrrolidinomethyl-4H-1,2,4-triazole;
4-[4-bromo-2-(2-pyridinecarbonyl)phenyl]-3-piperidinomethyl-4H-1,2,4-triazole;
4-[4-bromo-2-(2-pyridinecarbonyl)phenyl]-5-methyl-3-piperidinomethyl-4H-1,2,4-triazole;
4-[4-bromo-2-(2-pyridinecarbonyl)phenyl]-3-morpholinomethyl-4H-1,2,4-triazole;
4-[4-bromo-2-(2-pyridinecarbonyl)phenyl]-5-methyl-3-morpholinomethyl-4H-1,2,4-triazole;
4-[4-bromo-2-(2-pyridinecarbonyl)phenyl]-3-piperazinylmethyl-4H-1,2,4-triazole;
4-[4-bromo-2-(2-pyridinecarbonyl)phenyl]-5-methyl-3-(4-methyl-piperazinyl)methyl-4H-1,2,4-triazole;
4-[4-bromo-2-(2-pyridinecarbonyl)phenyl]-5-ethyl-3-(4-methylpiperazinyl)methyl-4H-1,2,4-triazole;
4-[4-bromo-2-(2-pyridinecarbonyl)phenyl]-3-(4-ethylpiperazinyl)methyl-4H-1,2,4-triazole;
4-[4-bromo-2-(2-pyridinecarbonyl)phenyl]-3-(4-ethylpiperazinyl)methyl-5-methyl-4H-1,2,4-triazole;
4-[4-bromo-2-(2-pyridinecarbonyl)phenyl]-3-[4-(2-hydroxyethyl)piperazinyl]methyl-4H-1,2,4-triazole;
4-[4-bromo-2-(2-pyridinecarbonyl)phenyl]-3-hexamethyleneiminomethyl-5-methyl-4H-1,2,4-triazole;
4-[4-bromo-2-(2-pyridinecarbonyl)phenyl]-3-(1-dimethylamino)-ethyl-4H-1,2,4-triazole;
4-[4-bromo-2-(4-pyridinecarbonyl)phenyl]-3-dimethylaminomethyl-4H-1,2,4-triazole;
4-[4-bromo-2-(4-pyridinecarbonyl)phenyl]-3-diethylaminomethyl-4H-1,2,4-triazole;
3-benzylaminomethyl-4-[4-bromo-2-(2-pyridinecarbonyl)phenyl]-4H-1,2,4-triazole;
3-benzylaminomethyl-4-[4-bromo-2-(2-pyridinecarbonyl)phenyl]-5-methyl-4H-1,2,4-triazole;
4-[4-bromo-2-(2-pyridinecarbonyl)phenyl]-3-dimethylaminomethyl-5-phenyl-4H-1,2,4-triazole;
5-benzyl-4-[4-bromo-2-(2-pyridinecarbonyl)phenyl]-3-dimethylaminomethyl-4H-1,2,4-triazole;
4-[2,4-dibromo-6-(2-pyridinecarbonyl)phenyl]-3-dimethylaminomethyl-4H-1,2,4-triazole;
4-[4-chloro-2-(2-pyridinecarbonyl)phenyl]-3-dimethylaminomethyl-4H-1,2,4-triazole;
4-[4-chloro-2-(2-pyridinecarbonyl)phenyl]-5-methyl-3-dimethylaminomethyl-4H-1,2,4-triazole;
4-[4-chloro-2-(2-pyridinecarbonyl)phenyl]-3-methylaminomethyl-4H-1,2,4-triazole;
4-[4-chloro-2-(2-pyridinecarbonyl)phenyl]-3-pyrrolidinomethyl-4H-1,2,4-triazole;
4-[4-chloro-2-(2-pyridinecarbonyl)phenyl]-5-methyl-3-pyrrolidinomethyl-4H-1,2,4-triazole;
4-[4-chloro-2-(2-pyridinecarbonyl)phenyl]-3-piperidinomethyl-4H-1,2,4-triazole;
4-[4-chloro-2-(2-pyridinecarbonyl)phenyl]-5-methyl-3-piperidinomethyl-4H-1,2,4-triazole;
4-[4-chloro-2-(2-pyridinecarbonyl)phenyl]-3-morpholinomethyl-4H-1,2,4-triazole;
4-[4-chloro-2-(2-pyridinecarbonyl)phenyl]-5-methyl-3-morpholinomethyl-4H-1,2,4-triazole;
4-[4-chloro-2-(2-pyridinecarbonyl)phenyl]-3-(4-methylpiperazinyl)methyl-4H-1,2,4-triazole;
4-[4-chloro-2-(2-pyridinecarbonyl)phenyl]-5-methyl-3-(4-methylpiperazinyl)methyl-4-1,2,4-triazole;
4-[4-chloro-2-(2-pyridinecarbonyl)phenyl-3-diethylaminomethyl-4H-1,2,4-triazole;
3-dimethylaminomethyl-4-[4-methyl-2-(2-pyridinecarbonyl)-phenyl]-4H-1,2,4-triazole;
3-dimethylaminomethyl-4-[4-methoxy-2-(2-pyridinecarbonyl)-phenyl]-4H-1,2,4-triazole;
3-dimethylaminomethyl-4-[4-nitro-2-(2-pyridinecarbonyl)phenyl]-4H-1,2,4-triazole;
3-dimethylaminomethyl-4-[2-(2-pyridinecarbonyl)phenyl-4-trifluoromethyl]-4H-1,2,4-triazole;

The present invention is illustrated in more detail below with reference to Preparative Examples and Examples, but the invention is not limited to the Examples.

PREPARATIVE EXAMPLE 1 a. A mixture of 8.7 g of 2-(2-amino-5-bromobenzoyl)-pyridine, 5.7 g of ortho-methyl-acetate, 2.8 ml. of acetic acid and 100 ml. of benzene is refluxed, while removing alcohol formed by azeotropic distillation, for 1.5 hours and then cooled. The resultant is washed with saturated aqueous sodium hydrogen carbonate, then with water, and dried over sodium sulfate. Evaporation of the solvent under reduced pressure gives 2-[2-(1-methoxyethylideneamino)-5-bromobenzoyl]-pyridine as oily product. This product is dissolved in 60 ml. methanolic solution and 44 ml. of hydrazine hydrate (100%) and 1.9 ml. of acetic acid are added to the solution. The mixture is stirred at room temperature for 3 hours and the precipitate formed is collected by filtration, washed with methanol and dried to give 3-amino-6-bromo-3,4-dihydro-4-hydroxy-2-methyl-4-(2-pyridyl)quinazoline as crystals. Recrystallization from a mixture of methanol and chloroform gives colorless crystals, melting at 208° to 210° C (decomposition).

Elemental analysis for $C_{14}H_{13}BrN_4O$: Calculated: C 50.46, H, 3.93, N 16.82: Found: C 50.02, H 3.70, N 17.11.

b. To a solution of 3.33 g of the thus prepared 3-amino-6-bromo-3,4-dihydro-4-hydroxy-2-methyl-4-(2-pyridyl)-quinazoline in 30 ml. of dimethylformamide is added with stirring under ice-cooling a solution of 0.51 g. of monochloroacetic acid anhydride in 6 ml. of dimethylformamide. After the mixture is stirred for 30 minutes, a solution of 4.2 g of potassium carbonate in 250 ml. of water is added thereto. The resulting mixure is filtered through a celite layer to remove insoluble material. The filtrate is extracted with ethyl acetate, and the ethyl acetate layer is wahsed with water, dried over sodium sulfate and then subjected to evaporation of the solvent. To the residue is added a mixture of ethyl acetate and ether, and the precipitate is collected by filtration to give mono-(chloroacetyl) derivative of the starting compound as crystals. Recrystallization from ethyl acetate gives colorless prisms, melting at 129 to 131° C (decomposition).

Elemental analysis for $C_{16}H_{14}BrClN_4O_2$: Calculated: C 46.90, H 3.44, N 13,68: Found: C 47.07, H 3.20, N 13.61.

c. A solution of 2.17 g of the mono(chloroacetyl) derivative of 3-amino-6-bromo-3,4-dihydro-4-hydroxy-2-methyl-4-(2-pyridyl)-quinazoline prepared in the experiment (b) in 30 ml. of acetic acid is heated at 80° C for 3 hours and then acetic acid is evaporated under reduced pressure. The residue is dissolved in chloroform, washed with saturated aqueous sodium hydrogen carbonate solution and water in this order and dried over sodium sulfate. After evaporation of the solvent under reduced pressure, the residue is washed with ethyl acetate and collected by filtration to give 4-[4-bromo-2-(2-pyridinecarbonyl)phenyl]-3-chloromethyl-5-methyl-4H-1,2,4-triazole as crystals. Recrystallization from a mixture of benzene-ether gives colorless prisms, melting at 170° at 171.5° C (decomposition).

Elemental analysis for $C_{16}H_{12}BrClN_4O$: Calculated: C 49.06, H 3.09, N 14.31: Found: C 48.85, H 2.89, N 14.15.

PREPARATIVE EXAMPLE 2 a. A mixture of 14 g of 2-(2-amino-5-bromobenzoyl)-pyridine and 42 ml. of formic acid (99%) is refluxed for one hour and then the solvent is evaporated. The residue is neutralized with saturated aqueous sodium hydrogen carbonate solution and the precipitated crystals of 2-(5-bromo-2-formamidobenzoyl)pyridine are collected by filtration, followed by washing with water. Recrystallization from methanol gives yellow needles, melting at 116° to 117° C.

Elemental analysis for $C_{13}H_9BrN_2O$: Calculated: C 51.17, H 2.97, N 9.18: Found: C 51.12, H 2.75, N 9.14.

b. To a solution of 11.2 g of the above 2-(5-bromo-2-formamidobenzoyl)pyridine in 50 ml. of methanol is added 10 ml. of hydrazine hydrate (100%). The resulting mixture is heated at 60° C for several minutes and thereafter left to stand at room temperature for 5 hours. The precipitate formed is collected by filtration and washed with methanol and ether to give 3-amino-6-bromo-4l -hydroxy-4-(2-pyridyl)-3,4-dihydroquinazoline as crystals (colorless granules), melting at 185° to 187° C (decomposition).

Elemental analysis for $C_{13}H_{11}BrN_4O$: Calculated: C 48.92, H 3.47, N 17.55: Found: C 48.77, H 3.35, N 17.56.

c. To 8.5 g of the above 3-amino-6-bromo-4-hydroxy-4-(2-pyridyl)-3,4-dihydroquinazoline are added 60 ml. of chloroform and a solution of 11.3 g of sodium carbonate in 110 ml. of water. To the resulting mixture is added dropwise 12 g of monochloroacetyl chloride under stirring at 10° to 15° C. The mixture is stirred at the same temperature for 30 minutes. The precipitated crystals are collected by filtration, followed by washing with chloroform and water in this order, and dried to give di-(chloroacetyl) derivative of the starting compound as crystals. Recrystallization from chloroform-methanol gives colorless prisms, melting at 148.5° to 149° C (decomposition).

Elemental analysis for $C_{17}H_{13}BrCl_2N_4O_3$: Calculated: C 43.24, H 2.77, N 11.86: Found: C 42.80, H 2.48, N 11.47.

A mixture of a solution of 0.94 g of the thus obtained di-(chloroacetyl) derivative of 3-amino-6-bromo-4-hydroxy-4-(2-pyridyl)-3,4-dihydroquinazoline in 19 ml. of benzene and 0.4 g of monochloroacetic acid is refluxed for 30 minutes. Then, the resulting benzene layer is washed with water and separated from the mixture. After evaporation of benzene under reduced pressure, the residue is washed with a mixture of methanol and isopropyl ether to give 4-[4-bromo-2-(2-pyridinecarbonyl)phenyl]-3-chloromethyl-4H-1,2,4-triazole as crystals. Recrystallization from ethyl acetate gives colorless crystals, melting at 146° to 147° C.

Elemental analysis for $C_{15}H_{10}BrClN_4O$: Calculated: C 47.70, H 2.66, N 14.83: Found: C 47.86, H 2.43, N 14.83.

PREPARATIVE EXAMPLE 3

To a solution of 0.7 g of 8-bromo-1-methyl-6-(2-pyridyl)-4H-s-triazolo[4,3-a][1,4]benzodiazepine in 5 ml. of 6 N-hydrochloric acid is added a solution of 1.25 g of sodium nitrite in 2.5 ml. of water at 5° to 10° C under ice-cooling. After stirring the mixture for one hour under cooling and another two hours at room temperature, the resulting mixture is neutralized with saturated aqueous sodium hydrogen carbonate solution and then extracted with chloroform. The chloroform layer is washed with water and dried over sodium sulfate. Evaporation of the solvent gives a mixture of 4-[4-bromo-2-(2-pyridinecarbonyl)phenyl]-3-hydroxymethyl-5-methyl-4H-1,2,4-triazole and 4-[4-bromo-2-(2-pyridinecarbonyl)-phenyl]-3-chloromethyl-4H-1,2,4-triazole.

The whole mixture as obtained above is dissolved in 20 ml. of chloroform and 4.0 ml. of thionyl chloride is added to the resulting solution. After the mixture is stirred at room temperature for 3 hours, the solvent is evaporated. To the residue is added saturated aqueous sodium hydrogen carbonate solution, and the mixture is extracted with chloroform. The chloroform layer is washed with water and dried over sodium sulfate. Evaporation of the solvent gives 4-[4-bromo-2-(2-pyridinecarbonyl)phenyl]-3-chloromethyl-5-methyl-4H-1,2,4-triazole as colorless crystals, melting at 172° to 173° C (decomposition). This product is identical with that obtained in Example 1(c).

The 3-hydroxymethyl derivative produced in the above experiment can easily be separated from the 3-chloromethyl derivative by subjecting the mixture to chromatography through a column of silica gel, using a mixture of chloroform-ethyl acetate-methanol (85 : 10 : 5) as an eluent. Recrystallization of the former 3-hydroxymethyl derivative from methanol gives colorless prisms melting at 203° to 205° C (decomposition).

PREPARATIVE EXAMPLE 4

To a solution of 2.50 g of 8-bromo-6-(2-pyridyl)-4H-s-triazolo[4,3-a][1,4]benzodiazepine in 20 ml. of 6 N-hydrochloric acid is added a solution of 5.0 g of sodium nitrite in 10 ml. of water at 5° to 10° C under ice-cooling. After stirring the mixture at 1.5 hours, the resulting mixture is neutralized with saturated aqueous sodium hydrogen carbonate solution and extracted with chloroform. The chloroform layer is washed with water and dried over sodium sulfate. Evaporation of the solvent gives a mixture of 4-[4-bromo-2-(2-pyridinecarbonyl)-phenyl]-3-hydroxymethyl-4H-1,2,4-triazole and 4-[4-bromo-2-(2-pyridinecarbonyl)-phenyl]-3-chloromethyl-4H-1,2,4-triazole. The mixture is dissolved in 50 ml. of chloroform and then 14 ml. of thionyl chloride is added to the solution. After the mixture is stirred at room temperature for 2 hours, the solvent is evaporated. The residue is neutralized with saturated aqueous sodium hydrogen carbonate solution, and extracted with chloroform. The chloroform layer is washed with water and dried over sodium sulfate, followed by evaporation of the solvent to give 4-[4-bromo-2-(2-pyridinecarbonyl)-phenyl]-3-chloromethyl4H-1,2,4-triazole as colorless crystals, melting at 147° to 149° C. This product is identical with that obtained in Example 2(d).

PREPARATIVE EXAMPLE 5

According to the same procedure as described in the preparative Example 4, the reaction product of 8-bromo-1-ethyl-6-(2-pyridyl)-4H-s-triazolo[4,3-a][1,4]benzodiazepine with 6 N-hydrochloric acid-sodium nitrite is chlorinated with thionyl chloride to give 4-[4-bromo-2-(2-pyridinecarbonyl)phenyl]-3-chloromethyl-5-ethyl-4H-1,2,4-triazole as crystals. Recrystallization from acetone gives pale yellow prisms, melting at 199° to 201° (decomposition).

EXAMPLE 1

A mixture of 0.25 g of 4-[4-bromo-2-(2-pyridinecarbonyl)phenyl]-3-chloromethyl-4H-1,2,4-triazole, 10 ml. of ethanol and 0.5 ml. of dimethylamine is refluxed for 1.5 hours. After evaporation of the solvent, the residue is diluted with water and then extracted with chloroform. The chloroform layer is washed with water, dried over sodium sulfate and then the solvent is evaporated. The residue is subjected to chromatography through a column of silica gel (15 g) using a mixture of chloroform-methanol-ethyl acetate (85 : 10 : 5) as an eluent to give 4-[4-bromo-2-(2-pyridinecarbonyl)phenyl]-3-dimethylaminomethyl-4H-1,2,4-triazole as crystals. Recrystallization from a mixture of acetone and n-hexane gives colorless prisms, melting at 145° to 146° C.

Elemental analysis for $C_{17}H_{16}BrN_5O$: Calculated: C 52.86, H 4.18, N 18;13: Found: C 52.74, H 4.10, N 18.12.

EXAMPLE 2

A mixture of 0.25 g of 4-[4-bromo-2-(2-pyridinecarbonyl)phenyl]-3-chloromethyl-5-methyl-4H-1,2,4-triazole, 10 ml. of ethanol and 0.5 ml. of dimethylamine is refluxed for 1.5 hours. After evaporation of the solvent, the residue is diluted with water and extracted with chloroform. The chloroform extract is washed with water, dried over sodium sulfate, followed by evaporation of the solvent to give 4-[4-bromo-2-(2-pyridinecarbonyl)phenyl]-3-dimethylaminomethyl-5-methyl-4H-1,2,4-triazole as colorless crystals. Recrystallization from a mixture of acetone and n-hexane gives colorless prisms, melting at 127° to 128° C.

Elemental analysis for $C_{18}H_{18}BrN_5O$: Calculated: C 54.01, H 4.53, N 17.50: Found: C 53.70, H 4.55, N 17.42.

According to the same procedures as in the foregoing Examples, the following compounds are produced from reactions between the corresponding compounds of the general formula (II) and (III):

4-[4-bromo-2-(2-pyridinecarbonyl)phenyl]-3-dimethylaminomethyl-5-ethyl-4H-1,2,4-triazole: colorless prisms (recrystallized from acetone), melting at 168° to 169° C;

3-benzylaminomethyl-4-[4-bromo-2-(2-pyridinecarbonyl)-phenyl]-5-methyl-4H-1,2,4-triazole: colorles granules (recrystallized from ether), melting at 117° to 118° C;

4-[4-bromo-2-(2-pyridinecarbonyl)phenyl]-3-morpholinomethyl-4H-1,2,4-triazole: colorless prisms (recrystallized from a mixture of acetone-n-hexane), melting at 166° to 167° C;

4-[4-bromo-2-(2-pyridinecarbonyl)phenyl]-5-ethyl-3-(4-methylpiperazinyl)methyl-4H-1,2,4-triazole: colorless prisms (recrystallized from acetone-n-hexane), melting at 174° to 175° C;

4-[4-bromo-2-(2-pyridinecarbonyl)phenyl]-5-ethyl-3-pyrrolidinomethyl-4H-1,2,4-triazole: colorless prisms (recrystallized from acetone), melting at 180° to 181° C.

EXAMPLE 3 an example of practical recipe in which a compound of this invention is utilized as tranquilizer is as follows:

| Tablet | | |
|---|---|---|
| (1) 4-[4-bromo-2-(2-pyridinecarbonyl)phenyl]-3-dimethylaminomethyl-5-methyl-4H-1,2,4-triazole | 1 mg | |
| (2) lactose | 73 mg | |
| (3) corn starch | 40 mg | |
| (4) hydroxypropyl cellulose | 5.5 mg | |
| (5) magnesium stearate | 0.5 mg | |
| | 120.0 mg per tablet | |

(1) (2), 9/10 quantity of (3), and (4) are thoroughly mixed and the mixture is granulated by wet granulation method. Remaining quantity of (3), and (5) are added to the granules and compressed into tablets. Thus prepared tablets may further be coated with suitable coating materials, e.g. sugar.

What we claim is:
1. A compound of the formula

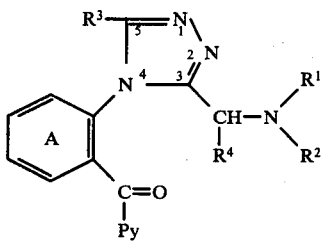

wherein R¹ and R², which may be the same or different, represent a $C_1$–$C_6$ alkyl group, a $C_3$–$C_6$ cycloalkyl group or a benzyl or phenethyl group, and one of R¹ and R² may be hydrogen atoms or R¹ and R² form a heterocyclic ring together with the nitrogen atom adjacent thereto selected from the group consisting of pyrrolidine, piperidine, piperazine, morpholine and N-substituted piperazines selected from the group consisting of N—$C_1$—$C_2$ alkyl piperazines, N-(2-hydroxy ethyl)-piperazine and homopiperidine; R³ represents hydrogen, a $C_1$–$C_6$ alkyl group, a $C_3$–$C_6$ cycloalkyl group, a benzyl or phenthyl group or an aryl group selected from the group consisting of phenyl, tolyl and naphthyl; R⁴ represents hydrogen or a $C_1$–$C_4$ alkyl group; Py represents a pyridyl group and the ring A is either unsubstituted or substituted by a halogen, nitro, a $C_1$–$C_4$ alkyl group, a $C_1$–$C_4$ alkoxy group or a trilfluoromethyl group or a pharmaceutically acceptable acid addition salt thereof.

2. A compound as claimed in claim 1, wherein each of R¹ and R² is lower alkyl group having 1 to 6 carbon atoms and the other is hydrogen atom.

3. A compound as claimed in claim 1, wherein each of R¹ and R² is lower alkyl groups having 1 to 6 carbon atoms.

4. A compound as claimed in claim 1, wherein R¹ and R² form a heterocyclic ring together with the nitrogen atom adjacent thereto.

5. A compound as claimed in claim 2, wherein R³ is hydrogen atom or a lower alkyl group having 1 to 3 carbon atoms.

6. A compound as claimed in claim 5, wherein R⁴ is hydrogen atom.

7. A compound as claimed in claim 6, wherein Py is 2-pyridyl group.

8. A compound as claimed in claim 7, wherein the ring A is substituted by a halogen atom.

9. A compound as claimed in claim 8, wherein the halogen atom is substituted in the 2-position of the ring A.

10. A compound as claimed in claim 9, wherein the halogen atom is bromine or chlorine.

11. A compound as claimed in claim 1, wherein R¹ and R² form piperidine ring together with the nitrogen atom adjacent thereto.

12. A compound as claimed in claim 1, wherein R¹ and R² form morpholine ring together with the nitrogen atom adjacent thereto.

13. A compound as claimed in claim 1, wherein R³ is hydrogen atom.

14. A compound as claimed in claim 1, wherein R³ is lower alkyl group having 1 to 3 carbon atoms.

15. A compound as claimed in claim 1, wherein R⁴ is hydrogen atom.

16. A compound as claimed in claim 1, wherein Py is 2-pyridyl group.

17. A compound as claimed in claim 1 wherein the ring A is substituted by a halogen in the 2-position.

18. A compound according to claim 1, namely 4-[4-bromo2-(2-pyridinecarbonyl)phenyl]-3-dimethylaminomethyl-4H-1,2,4triazole.

19. A compound according to claim 1, namely 4-[4-bromo2-(2-pyridinecarbonyl)phenyl]-3-dimethylaminomethyl-5-methyl4H-1,2,4-triazole.

20. A compound according to claim 1, namely 4-[4-bromo2-(2-pyridinecarbonyl)phenyl]-3-dimethylaminomethyl-5-ethyl4H-1,2,4-triazole.

21. A compound according to claim 1, namely 3-benzylaminomethyl-4-[4-bromo-2-(2-pyridinecarbonyl)-phenyl-5-methyl4H-1,2,4-triazole.

22. A compound according to claim 1, namely 4-[4-bromo2-(2-pyridinecarbonyl)phenyl]-3-morpholinomethyl-4H-1,2,4triazole.

23. A compound according to claim 1, namely 4-[4-bromo2-(2-pyridinecarbonyl)phenyl]-5-ethyl-3-(4-methylpiperazinyl)methyl-4H-1,2,4-triazole.

24. A compound according to claim 1, namely 4-[4-bromo2-(2-pyridinecarbonyl)phenyl]-5-ethyl-3-pyrrolidinomethyl-4H1,2,4-triazole.

25. A pharmaceutical compound having central nervous system activity comprising a therapeutically effective amount of a compound selected from the group consisting of a compound as claimed in claim 1 or a pharmaceuticaly acceptable acid addition salt thereof together with a pharmaceutically acceptable carrier or diluent therefor.

* * * * *

UNITED STATES PATENT OFFICE
CERTIFICATE OF CORRECTION

Patent No. 4,044,129   Dated August 23, 1977

Inventor(s) Yutaka Kuwada, et al

It is certified that error appears in the above-identified patent and that said Letters Patent are hereby corrected as shown below:

In the Abstract, line 2 from bottom: "as for example" should be --system, as, for example, --.

Column 1, line 37: "transquilizers" should be --tranquilizers--.

Column 7, line 34: "wahsed" should be --washed--.

line 43: "13,68" should be --13.68--.

Column 8, line 14: "bromo-41  -hydroxy" should be --bromo-4-hydroxy --.

Column 9, line 42: "chloromethyl4H" should be --chloromethyl-4H --.

UNITED STATES PATENT OFFICE
CERTIFICATE OF CORRECTION

Patent No. 4,044,129  Dated August 23, 1977

Inventor(s) Yutaka Kuwada, et al

It is certified that error appears in the above-identified patent and that said Letters Patent are hereby corrected as shown below:

Column 10, line 5: "18;13" should be --18.13--.

line 31: "colorles" should be --colorless--.

Column 12, line 27: "methyl4H" should be --methyl-4H --.

lines 26 and 29: "bromo2" should be --bromo-2 --.

line 30: "ethyl4H" should be --ethyl-4H --.

Signed and Sealed this

Twenty-fourth Day of January 1978

[SEAL]

Attest:

RUTH C. MASON  
Attesting Officer

LUTRELLE F. PARKER  
Acting Commissioner of Patents and Trademarks